(12) United States Patent
Talaat

(10) Patent No.: US 10,054,586 B2
(45) Date of Patent: Aug. 21, 2018

(54) BIOMARKERS FOR EARLY DIAGNOSIS AND DIFFERENTIATION OF MYCOBACTERIAL INFECTION

(71) Applicant: Wisconsin Alumni Research Foundation, Madison, WI (US)

(72) Inventor: Adel M. Talaat, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/923,478

(22) Filed: Oct. 27, 2015

(65) Prior Publication Data
US 2016/0123979 A1  May 5, 2016

Related U.S. Application Data

(60) Provisional application No. 62/069,520, filed on Oct. 28, 2014.

(51) Int. Cl.
| | |
|---|---|
| *A61K 39/04* | (2006.01) |
| *A61K 39/02* | (2006.01) |
| *G01N 33/53* | (2006.01) |
| *G01N 33/569* | (2006.01) |
| *C12Q 1/689* | (2018.01) |

(52) U.S. Cl.
CPC ......... *G01N 33/5695* (2013.01); *C12Q 1/689* (2013.01); *G01N 33/56933* (2013.01); *C12Q 2600/158* (2013.01); *G01N 2333/30* (2013.01); *G01N 2469/10* (2013.01); *G01N 2469/20* (2013.01)

(58) Field of Classification Search
CPC ........ A61K 39/00; A61K 39/04; G01N 33/53; G01N 33/5695
USPC ........ 424/234.1, 248.1; 435/4, 7.1, 7.2, 7.32
See application file for complete search history.

(56) References Cited

U.S. PATENT DOCUMENTS

| | | |
|---|---|---|
| 2007/0042383 A1 | 2/2007 | Kapur |
| 2010/0159485 A1 | 6/2010 | Mukhopadhyay et al. |
| 2014/0271719 A1 | 9/2014 | Talaat |

FOREIGN PATENT DOCUMENTS

| | | |
|---|---|---|
| WO | 2005001092 A2 | 1/2005 |
| WO | 20100132054 A1 | 11/2010 |
| WO | 2014164055 A1 | 10/2014 |

OTHER PUBLICATIONS

Seth, M., et al. Biomarker Discovery in Subclinical Mycobacterial Infections of Cattle. PLoS One, vol. 4, Issue 5, e5478, May 2009.*
Brust, B., et al. *Mycobacterium tuberculosis* Lipolytic enzymes as Potential Biomarkers for the Diagnosis of Active Tuberculosis. PLoS One, vol. 6, Issue 9, e25078, Sep. 2011.*
International Searching Authority, Invitation to Pay Additional Fees and Where Applicable, Protest Fee; in the matter of PCT/US2015/057596; dated Jan. 26, 2016.
Al-Khodari, et al. (2011). Identification, Diagnostic Potential, and Natural Expression of Immunodominant Seroreactive Peptides Encoded by Five *Mycobacterium tuberculosis*-Specific Genomic Regions. Clinical and Vaccine Immunology 18, 477-482.
Bezos, et al. (2010). Experimental infection with *Mycobacterium caprae* in goats and evaluation of immunological status in tuberculosis and paratuberculosis co-infected animals. Veterinary Immunology and Immunopathology 133, 269-275.
Collins, et al. (1994). Herd prevalence and geographic distribution of, and risk factors for, bovine paratuberculosis in Wisconsin. J Am Vet Med Assoc 204:636-641.
Daniel, et al. (2009). Outbreak of tuberculosis caused by *Mycobacterium bovis* in golden Guernsey goats in Great Britain. Vet rec 19;165, 335-342.
Gey Van Pittius, et al. (2012). Infection of African Buffalo (*Syncerus gaffer*) by Oryx Bacillus, a Rare Member of the Antelope Clade of the *Mycobacterium tuberculosis* Complex. Journal of Wildlife Diseases 48, 849-857.
Ghosh, et al. (2014). Virulence and Immunity Orchestrated by the Global Gene Regulator sigL in *Mycobacterium avium* subsp. *paratuberculosis*. Infect Immun 82:3066-3075.
Ghosh, et al. (2013). Key Role for the Alternative Sigma Factor, SigH, in the Intracellular Life of *Mycobacterium avium* subsp. *paratuberculosis* during Macrophage Stress. Infect. Immun. 81:2242-2257.
Hahn, et al. (2005). The *Mycobacterium tuberculosis* extracytoplasmic-function sigma factor SigL regulates polyketide synthases and secreted or membrane proteins and is required for virulence. Journal of Bacteriology. 187:7062-7071.
Harlow, et al. (1988) Antibodies: A Laboratory Manual, Cold Spring Harbor Laboratory Press, Cold Spring Harbor, N.Y.
Li, et al. (2005). The complete genome sequence of *Mycobacterium avium* subspecies *paratuberculosis*. Proceedings of the National Academy of Sciences of the United States of America 102:12344-12349.
Linnabary, et al. (2001). Johne's disease in Cattle. Council for Agricultural Science and Technology 17:1-10.
Park, et al. (2008). Regulation of the SigH stress response regulon by an essential protein kinase in *Mycobacterium tuberculosis*. Proceedings of the National Academy of Sciences U.S.A. 105:13105-13110.
Xi, et al. (2011). A novel strategy to screen Bacillus Calmette-Guerin protein antigen recognized by gammadelta TCR. PLoS One 6, e18809.
Verma, et al., Profiling of ABC Transporters During Active Ulcerative Colitis and In Vitro Effect of Inflammatory Modulators, Dig. Dis. Sci., 2013, 58:2282-2292.

(Continued)

*Primary Examiner* — Rodney P Swartz
(74) *Attorney, Agent, or Firm* — Quarles & Brady LLP

(57) ABSTRACT

Mycobacterial-specific biomarkers and methods of using such biomarkers for diagnosis of mycobacterial infection in a mammal are disclosed.

**10 Claims, 2 Drawing Sheets
(1 of 2 Drawing Sheet(s) Filed in Color)**

(56) References Cited

OTHER PUBLICATIONS

Database Geneseq, *Mycobacterium paratuberculosis* Protein, SEQ ID 5577, XP-002752570, Jul. 10, 2008, 1 page.
PCT International Search Report and Written Opinion, PCT/US2015/057596, dated May 31, 2016, 21 pages.

* cited by examiner

BIOMARKERS FOR EARLY DIAGNOSIS AND DIFFERENTIATION OF MYCOBACTERIAL INFECTION

CROSS-REFERENCE TO RELATED APPLICATIONS

This application claims priority to U.S. Ser. No. 62/069,520, filed Oct. 28, 2014 and incorporated by reference herein.

STATEMENT REGARDING FEDERALLY SPONSORED RESEARCH

This invention was made with government support under 58-3148-0-174 awarded by the USDA/ARS and 2012-33610-19517 awarded by the USDA/NIFA. The government has certain rights in the invention.

BACKGROUND OF THE INVENTION

The field of the invention is vaccine and diagnostic biomarkers. More particularly, the invention relates to a set of biomolecules as diagnostic biomarkers for distinguishing between vaccinated and infected animals and between *M. ap.* and *M. bovis*.

Mycobacterial infections cause significant health problems to humans and animals including human tuberculosis, bovine tuberculosis, and Johne's disease. Johne's disease (aka *paratuberculosis*) is caused by infection with *Mycobacterium avium* subspecies *paratuberculosis* (*M. ap*); this disease causes severe economic losses estimated at $500 million per year for the US dairy industry alone, and these infections constitute a problem for 91% of dairy herds. Bovine tuberculosis, which is caused by infection with *M. bovis*, is endemic in dairy herds in several parts of the developing world and a significant problem for the wildlife animals in several developed countries (e.g., UK, USA, and Australia).

Current diagnostics can detect mycobacterial infections in cattle that have started to shed the bacteria or developed an antibody response. The available diagnostic tools are unreliable to detect early stages of infection or to differentiate infected from vaccinated animals (aka the DIVA principle). Early detection of mycobacterial infections is imperative to control the infection in herds. Further, the availability of a DIVA-based assay will facilitate adoption of new vaccines that can prevent *M. ap* infection.

Needed in the art are methods or diagnostic tools for detecting early stages of mycobacterial infection. Additionally, needed in the art are methods or diagnostic tools for distinguishing vaccinated from infected animals and distinguishing *M. ap.* from *M. bovis* pathogens in infected animals.

SUMMARY OF THE INVENTION

The present invention overcomes the aforementioned drawbacks by providing a set of pathogen and animal biomolecules for detecting mycobacterial infections in the early stage. By using the set of biomolecules as biomarkers, one can distinguish between vaccinated and infected animals, distinguish between *M. ap.* and *M. bovis* pathogens in infected animals, and distinguish *M. ap.* and *M. bovis* infections.

In one aspect, the present invention discloses a method for diagnosis of mycobacterial infection in a mammal. The method comprises the steps of (a) obtaining a sample from the mammal; (b) testing the sample for the concentration level of at least one mycobacterial-specific biomarker and comparing the level of the biomarker against the level detected in an uninfected mammalian sample; and (c) determining the infection status of the mammal.

In one embodiment, the method is used for early diagnosis and detection of mycobacterial infection in a mammal. In one embodiment, the testing is via ELISA assay for antibodies formed against the biomarker. In one embodiment, the sample is a blood sample.

In one embodiment, the mammal of the present invention is selected from the group consisting of bubaline, elephantine, musteline, pardine, phocine, rhinocerine, caprine, hircine, leonine, leporine, lupine, lyncine, murine, rusine, tigrine, ursine, vulpine, zebrine, vespertilionine, porcine, bovine, equine, swine, elaphine, ovine, caprine, camelidae, feline, cervine, primate, human and canine mammals. In one embodiment, the mammal is selected from the group of pig, cow, human, rodent, sheep, goat and deer. In one embodiment, the mammal is selected from the group consisting of cow, sheep and goat. In one specific embodiment, the mammal is a cow.

In one embodiment, the mycobacterial-specific biomarker used in the present method comprises at least one member selected from the group consisting of gene sequences Q73SF4, Q73Y73, Q73ZE6, Q73SL7, Q73VK6, Q73XZ0, Q740D1 and Q73UE0 and expression products derived thereof.

In one embodiment, the mycobacterial-specific biomarker used in the present method comprises at least one member selected from the group consisting of gene sequences Q73VL6, Q73YW9, Q741L4, Q744E5, Q73YP5, Q73WE5, Q73U21, Q73UH9, Q741M5, Q742F4, and Q73SU6 and expression products derived thereof.

In another embodiment, the present invention comprises host biomarkers listed in Table 3.

In one embodiment, the biomarker used in the present invention comprises a protein having at least 50%, 60%, 70%, 80%, or 90% of the amino acid sequence of *M. paratuberculosis* which is not conserved in *M. bovis*, as exemplified by the amino acid difference between *M. paratuberculosis* and *M. bovis* in FIG. 1.

In one aspect, the present invention discloses a method for differentiating a vaccinated mammal from a non-vaccinated mammal or from an infected mammals, the method comprising the steps of (a) obtaining a sample from the test mammal; (b) testing the sample for the concentration level of at least one of mycobacterial specific markers and comparing the level of the markers with that detected in an uninfected animal; and (c) determining the status of the mammal.

In one embodiment, the mammals are vaccinated with a *mycobacterium* mutant vaccine.

In one embodiment, the *mycobacterium* mutant vaccine comprises at least one mutation in at least one gene sequence encoding global gene regulators (GGRs) selected from the group consisting of sigH, sigL and LipN.

In one embodiment, the marker comprises at least one member selected from the group consisting of Q73SF4, Q73Y73, Q73ZE6, Q73SL7, Q73VK6, Q73XZ0, Q740D1 and Q73UE0 and expression products derived thereof.

In one embodiment, the marker comprises at least one member selected from the group consisting of Q73VL6, Q73YW9, Q741L4, Q744E5, Q73YP5, Q73WE5, Q73U21, Q73UH9, Q741M5, Q742F4, and Q73SU6 and expression products derived thereof.

In one embodiment, the marker comprises a protein having at least 50%, 60%, 70%, 80%, or 90% of the amino acid sequence of M. paratuberculosis which is not conserved in M. bovis as exemplified by the amino acid difference between M. paratuberculosis and M. bovis in FIG. 1.

In one aspect, the present invention discloses a method for differentiating a M. ap infected mammal from a M. bovis infected mammal, the method comprising the steps of (a) obtaining a sample from the test mammal; (b) testing the sample for the concentration level of at least one of mycobacterial-specific markers and comparing the level of the markers with that detected in a M. bovis infected mammal; and (c) determining the status of the mammal.

In one embodiment, the mycobacterial-specific markers comprise a protein having at least 50%, 60%, 70%, 80%, or 90% of the amino acid sequence of M. paratuberculosis which is not conserved in M. bovis.

In one aspect, the present invention discloses a set of biomarkers for early diagnosis and differentiation of mycobacterial infection. The biomarkers comprise at least one member selected from the group consisting of Q73SF4, Q73Y73, Q73ZE6, Q73SL7, Q73VK6, Q73XZ0, Q740D1 and Q73UE0 and expression products derived thereof.

In one embodiment, the biomarkers comprise at least two members selected from the group consisting of Q73SF4, Q73Y73, Q73ZE6, Q73SL7, Q73VK6, Q73XZ0, Q740D1 and Q73UE0 and expression products derived thereof.

In one aspect, the present invention discloses set of biomarkers for early diagnosis and differentiation of mycobacterial infection. The biomarkers comprise at least one member selected from the group consisting of Q73VL6, Q73YW9, Q741L4, Q744E5, Q73YP5, Q73WE5, Q73U21, Q73UH9, Q741M5, Q742F4, and Q73SU6 and encoded genes or expression products derived thereof.

In one embodiment, the biomarkers comprise at least two members selected from the group consisting of Q73VL6, Q73YW9, Q741L4, Q744E5, Q73YP5, Q73WE5, Q73U21, Q73UH9, Q741M5, Q742F4, and Q73SU6 and encoded genes or expression products derived thereof.

In one aspect, the present invention discloses a set of biomarkers for early diagnosis and differentiation of mycobacterial infection. The biomarkers comprise a protein having at least 50%, 60%, 70%, 80%, 90%, 95% or 100% of the amino acid sequence of M. paratuberculosis which is not conserved in M. bovis.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, reference is made therefore to the claims and herein for interpreting the scope of the invention.

BRIEF DESCRIPTION OF THE DRAWINGS

The patent or application file contains at least one drawing in color. Copies of this patent or patent application publication with color drawings will be provided by the Office upon request and payment of the necessary fee.

FIG. 1 is a graph showing the alignment plot of amino acids deduced from the protein sequence in LipN of both M. paratuberculosis and M. bovis. Peptides conserved in M. paratuberculosis sequence but absent from M. bovis are the target for developing the DIVA test.

DETAILED DESCRIPTION OF THE INVENTION

Figure 2A:
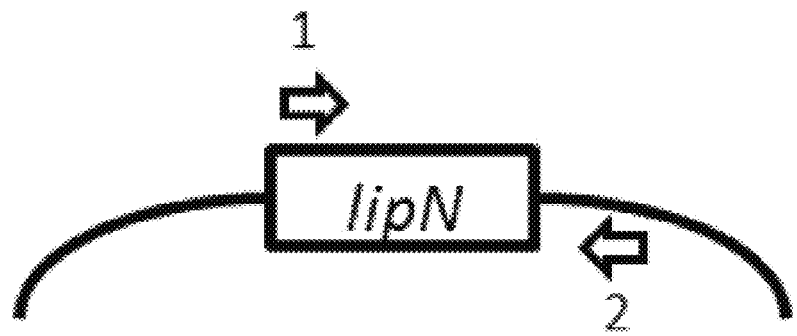
FIG. 2A is a diagram showing multiplex PCR strategy using 3 primers, specifically, Wild-type (virulent) strain with intact lipN gene.

The term "mycobacterium," as used herein, refers to a genus of actinobacteria given its own family, the mycobacteriaceae. The genus includes pathogens known to cause serious diseases in mammals, including tuberculosis (Mycobacterium tuberculosis) and leprosy (Mycobacterium leprae).

Mycobacterium tuberculosis complex (MTBC) members are causative agents of human and animal tuberculosis. Species in this complex may include M. tuberculosis, the major cause of human tuberculosis, M. bovis, M. bovis BCG, M. africanum, M. canetti, M. caprae, M. microti, and M. pinnipedii.

Mycobacterium avium complex (MAC) is a group of species that, in a disseminated infection but not lung infection, used to be a significant cause of death in AIDS patients. Species in this complex include M. avium, M. avium paratuberculosis, which has been implicated in Crohn's disease in humans and is the causative agent of Johne's disease in cattle and sheep, M. avium silvaticum, M. avium "hominissuis," M. colombiense, and M. indicus pranii.

Mycobacterial infections are notoriously difficult to treat. The organisms are hardy due to their cell wall, which is neither truly Gram negative nor positive. In addition, they are naturally resistant to a number of antibiotics that disrupt cell-wall biosynthesis, such as penicillin. Due to their unique cell wall, they can survive long exposure to acids, alkalis, detergents, oxidative bursts, lysis by complement, and many antibiotics. Most mycobacteria are susceptible to the antibiotics clarithromycin and rifamycin, but antibiotic-resistant strains have emerged.

The term "biomolecule," as used herein, refers to any organic molecule that is part of or from a living organism. Biomolecules may include nucleic acids, a nucleotide, a polynucleotide, an oligonucleotide, a peptide, a protein, a carbohydrate, a ligand, a receptor, among others. In one embodiment of the present invention, biomolecules may include genes and their expression products.

The term "expression product," as used herein, refers to any product produced during the process of gene expression. These products are often proteins, but in non-protein coding genes such as ribosomal RNA (rRNA), transfer RNA (tRNA) or small nuclear RNA (snRNA) genes, the product is a functional RNA.

The terms "polypeptide," "peptide," and "protein," as used herein, refer to a polymer comprising amino acid residues predominantly bound together by covalent amide bonds. The terms apply to amino acid polymers in which one or more amino acid residue may be an artificial chemical mimetic of a naturally occurring amino acid, as well as to naturally occurring amino acid polymers and non-naturally occurring amino acid polymers. As used herein, the terms may encompass amino acid chains of any length, including full length proteins, wherein the amino acids are linked by covalent peptide bonds. The protein or peptide may be isolated from a native organism, produced by recombinant techniques, or produced by synthetic production techniques known to one skilled in the art.

The term "recombinant protein," as used herein, refers to a polypeptide of the present disclosure which is produced by recombinant DNA techniques, wherein generally, DNA encoding a polypeptide is inserted into a suitable expression vector which is in turn used to transform a heterologous host cell (e.g., a microorganism or yeast cell) to produce the heterologous protein.

The term "recombinant nucleic acid" or "recombinant DNA," as used herein, refers to a nucleic acid or DNA of the present disclosure which is produced by recombinant DNA techniques, wherein generally, DNA encoding a polypeptide is inserted into a suitable expression vector which is in turn used to transform a host cell to produce the heterologous protein.

The term "mammal," as used herein, refers to any living species which can be identified by the presence of sweat glands, including those that are specialized to produce milk to nourish their young. In one embodiment, the mammal suitable for the present invention may include bubaline, elephantine, musteline, pardine, phocine, rhinocerine, caprine, hircine, leonine, leporine, lupine, lyncine, murine, rusine, tigrine, ursine, vulpine, zebrine, vespertilionine, porcine, bovine, equine, swine, elaphine, ovine, caprine, camelidae, feline, cervine, primate, human and canine mammals. In one preferred embodiment of the present invention, the mammal may be one of the ruminants such as cattle, goats, sheep, giraffes, yaks, deer, camels, llamas, antelope, and some macropods. In one specific embodiment of the present invention, the mammal may include any of the milk cattle species, such as cow, sheep and goat.

The term "antibody," as used herein, refers to a class of proteins that are generally known as immunoglobulins. The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

The term "marker" or "biomarker," as used herein, refers to a biomolecule (e.g., protein, nucleic acid, carbohydrate, or lipid) that is differentially expressed in the cell, differentially expressed on the surface of an infected cell, differentially phosphorylated, or differentially secreted by a infected cell in comparison to a normal cell or in a paracrine fashion by neighboring uninfected cells, and which is useful for the diagnosis of mycobacterial infection and for preferential targeting of a pharmacological agent to an infected mammal Often times, such markers are molecules that are overexpressed in an infected cell in comparison to a normal cell, for instance, at least 1-fold over-expression, at least 2-fold over-expression, at least 3-fold over-expression or more in comparison to a normal cell.

Figure 1:
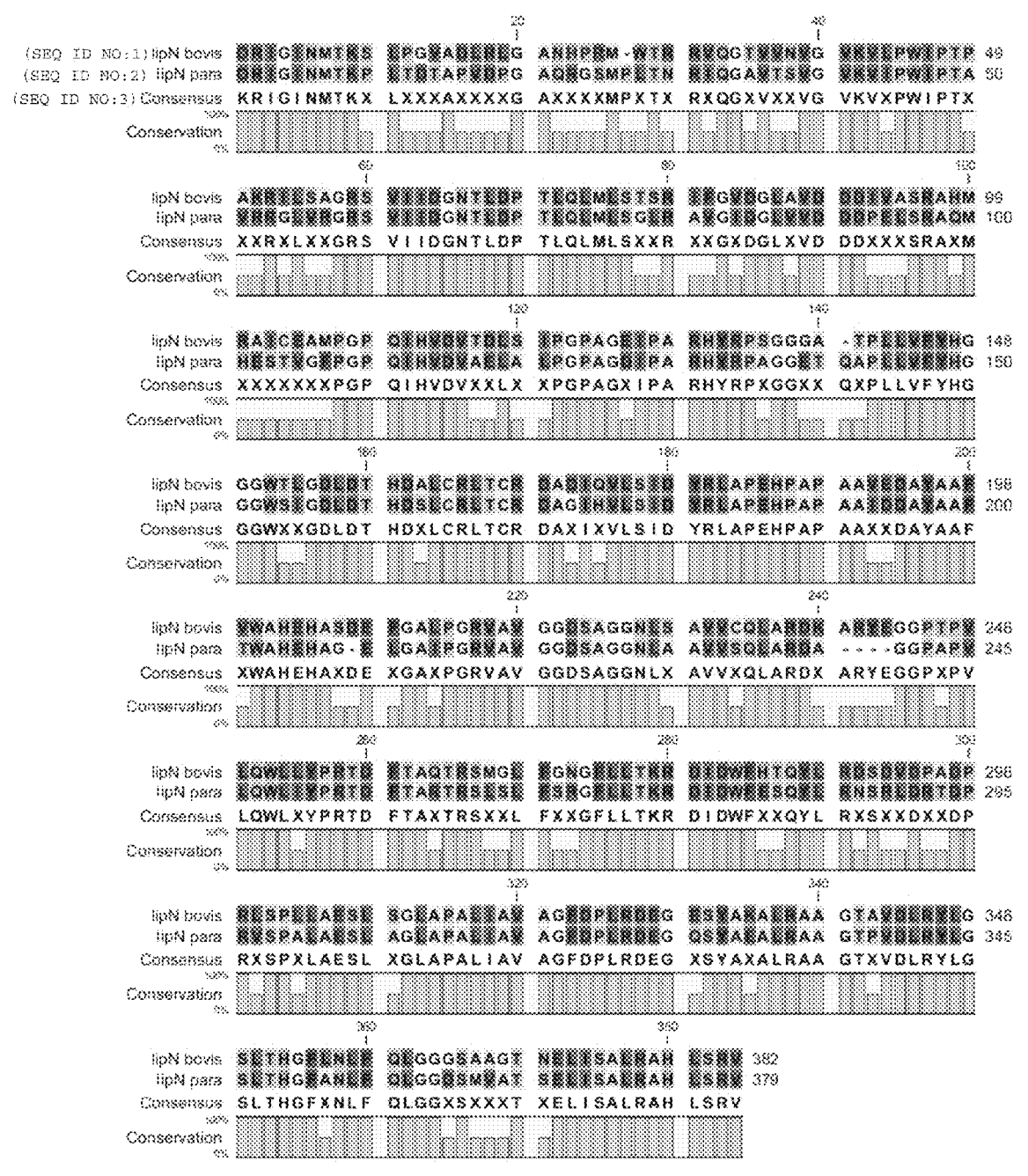

The term "mycobacterial-specific biomarkers," as used herein, refers to biomarkers which are specifically related to mycobacterial infection. Some of these biomarkers are listed at FIG. 1 and Tables 1 and 2.

The term "lyophilization," as used herein, refers to freezing of a material at low temperature followed by dehydration by sublimation, usually under a high vacuum. Lyophilization is also known as freeze drying. Many techniques of freezing are known in the art of lyophilization such as tray freezing, shelf freezing, spray-freezing, shell-freezing and liquid nitrogen immersion. Each technique will result in a different rate of freezing. Shell freezing may be automated or manual. For example, flasks can be automatically rotated by motor driven rollers in a refrigerated bath containing alcohol, acetone, liquid nitrogen, or any other appropriate fluid. A thin coating of product is evenly frozen around the inside "shell" of a flask, permitting a greater volume of material to be safely processed during each freeze drying run. Tray freezing may be performed by, for example, placing the samples in lyophilizer, equilibrating 1 hr at a shelf temperature of 0° C., then cooling the shelves at 0.5° C./min to −40° C. Spray-freezing, for example, may be performed by spray freezing into liquid, dropping by ~20 µl droplets into liquid $N_2$, spray freezing into vapor over liquid, or by other techniques known in the art.

The term "antigen," as used herein, refers to any molecule that is capable of eliciting an immune response, whether a cell-mediated or humoral immune response, whether in the presence or absence of an adjuvant. An antigen can be any type of molecule, e.g., a peptide or protein, a nucleic acid, a carbohydrate, a lipid, and combinations thereof. A "vaccine antigen" is an antigen that can be used in a vaccine preparation. A "therapeutic antigen" is an antigen that can be used for therapeutic purposes.

The term "vaccine," as used herein, refers to an antigenic preparation used to produce active immunity to a disease, in order to prevent or ameliorate the effects of infection. The antigenic moiety making up the vaccine may be either a live or killed microorganism, or a natural product purified from a microorganism or other cell including, but not limited to tumor cells, a synthetic product, a genetically engineered protein, peptide, polysaccharide or similar product or an allergen.

The term "immunologically active," as used herein, refers to the ability to raise one or more of a humoral response or a cell mediated response specific to an antigen.

The term "adjuvant," as used herein, refer to compounds that, when used in combination with specific vaccine antigens in formulations, augment or otherwise alter or modify the resultant immune responses. An adjuvant combined with a vaccine antigen increases the immune response to the vaccine antigen over that induced by the vaccine antigen alone. An adjuvant may augment humoral immune responses or cell-mediated immune responses or both humoral and cell-mediated immune responses against vaccine antigens.

The term "detecting," as used herein, refers to confirming the presence of the biomarker or marker present in the sample. Quantifying the amount of the biomarker or marker present in a sample may include determining the concentration of the biomarker present in the sample. Detecting and/or quantifying may be performed directly on the sample, or indirectly on an extract therefrom, or on a dilution thereof.

In one aspect, the present invention relates to a method for diagnosis of mycobacterial infection in a mammal. In one embodiment, the present invention discloses a method for early detection of mycobacterial infection. The term "early detection," as used herein, refers to detection of mycobacterial infection during the early stage of infection, e.g., a stage before the development of chronic diarrhea.

In another embodiment, the present invention discloses a method for differentiating a vaccinated mammal from a non-infected mammal or a mycobacterial infected mammal.

In another embodiment, the present invention discloses a method for differentiating mammals infected by one kind of mycobacteria from another kind of mycobacteria.

In one specific embodiment, the present invention discloses a method for differentiating a *M. ap* infected mammal from a *M. bovis* infected mammal.

The detection of mycobacterial infection and related diseases such as Johne's disease is very difficult because the disease generally takes many years to develop, and the organism is shed by the mammal periodically, so every mammal must be repeatedly tested over long time periods.

Applicants have identified mycobacterial-specific biomarkers, such as genes and/or expression products derived thereof, useful for detection of mycobacterial infection. Mycobacterial-specific biomarkers or a combination of such biomarkers may also be used to differentiate a vaccinated mammal (e.g., from genetically engineered vaccines) from a non-infected mammal or a mycobacterial-infected mammal. Further, mycobacterial-specific biomarkers or a combination of such biomarkers may also be used to differentiate one pathogen (e.g., *M. paratuberculosis*) from another pathogen (e.g., *M. bovis*) for infected mammals.

Differentiating Vaccinated Mammals from Mycobacterial-Infected Mammals

In one embodiment, the present invention discloses a method for differentiating a vaccinated mammal from a mycobacterial infected mammal.

In one embodiment, the method for differentiating a vaccinated mammal from a mycobacterial-infected mammal comprises the steps of (a) obtaining a sample from the mammal; (b) testing the sample for the concentration level of at least one mycobacterial-specific biomarker and comparing the level of the biomarker against the level detected in an uninfected mammalian sample; and (c) determining the infection status of the mammal.

A sample suitable for the present invention may include any biological sample from the mammal. The biological sample may include, without limitation, saliva, sputum, blood, plasma, serum, urine, feces, cerebrospinal fluid, amniotic fluid, wound exudate, or tissue of the subject of mammal. In one specific embodiment, the biological sample is a blood sample.

A major problem in employing mass vaccination program for the control of JD in dairy herds is the inability to differentiate between infected and vaccinated animals with the current vaccine (DIVA principal). Applicants have previously proposed using genetically engineered vaccines (PCT patent application US2014/02024). One would wish to consider the DIVA principal and wish to distinguish between *M. bovis* and JD vaccinated animals that have been vaccinated with genetically engineered vaccines.

In one embodiment, Applicants identify biomolecules as mycobacterial-specific biomarkers. For example, the biomolecules of mycobacterial-specific biomarkers may include genes and their expression products which are present in a *M. ap* wild-type strain but not present or have a low expression level in genetically engineered vaccines.

In another embodiment, the present invention comprises host biomarkers listed in Table 3.

Applicants envision that the present invention may be applicable to any genetically engineered vaccines. In one specific embodiment, the present invention is applicable to live attenuated vaccines. The example of the live attenuated vaccines may include sigL and sigH mutants. PCT patent application US2014/020248 discloses live attenuated vaccines, such as sigL and sigH mutants.

In one embodiment involving sigL and sigH mutants, the mycobacterial-specific biomarker may comprise at least one member selected from the group consisting of gene sequences Q73SF4, Q73Y73, Q73ZE6, Q73SL7, Q73VK6, Q73XZ0, Q740D1 and Q73UE0 and expression products derived thereof. In another embodiment, the mycobacterial-specific biomarker may comprise at least two, three, four, five, six, seven or eight members selected from the group consisting of gene sequences Q73 SF4, Q73Y73, Q73ZE6, Q73SL7, Q73VK6, Q73XZ0, Q740D1 and Q73UE0 and expression products derived thereof. Preferably, the mycobacterial-specific biomarker may comprise at least two members selected from the group as discussed above.

In one embodiment involving sigL and sigH mutants, the mycobacterial-specific biomarker comprises at least one member selected from the group consisting of gene sequences Q73VL6, Q73YW9, Q741L4, Q744E5, Q73YP5, Q73WE5, Q73U21, Q73UH9, Q741M5, Q742F4, and Q73SU6 and expression products derived thereof.

In one embodiment, the mycobacterial-specific biomarker comprises at least two, three, four, five, six, seven, eight, nine or ten members selected from the group consisting of gene sequences Q73VL6, Q73YW9, Q741L4, Q744E5, Q73YP5, Q73WE5, Q73U21, Q73UH9, Q741M5, Q742F4, and Q73SU6 and expression products derived thereof.

In one embodiment, the mycobacterial-specific biomarker comprises all gene sequences Q73VL6, Q73YW9, Q741L4, Q744E5, Q73YP5, Q73WE5, Q73U21, Q73UH9, Q741M5, Q742F4, and Q73SU6 and expression products derived thereof.

In one embodiment, the presence or absence of the biomarkers in a mammal may demonstrate the infection status of the mammal. In one specific embodiment, the biomarkers that are significantly over-expressed in the wild type strain and not in the mutant vaccine and could be used for the mutant vaccine-DIVA testing.

For example, when the biomarkers are those significantly over-expressed in animals infected with the wild type strain and not in the mutant vaccine, the presence of at least one biomarker in a mammal shows that the mammal may be infected and not merely vaccinated. On the other hand, the absence of at least one biomarker in a mammal shows that the mammal may be vaccinated.

In one embodiment, Applicants envision that the present invention is also applicable when antigens are inoculated to a mammal and the infection status of the mammal needs to be identified. Specifically, the infection status may include whether a mammal is vaccinated or whether a mammal is infected with *M. paratuberculosis* or *M. bovis*.

In one embodiment, Applicants envision that the present invention may also be used in a skin test. For example, Applicants envision that a mammal may be inoculated with a reagent comprising any suitable antigen or a biomarker as discussed herein, and skin induration of the mammal may be recorded. Skin induration may be used to differentiate infected from vaccinated animals.

Early Stage Detection Methods

In another embodiment, the concentration level of the biomarkers may be compared with the level detected in a standard sample, such as an uninfected mammalian sample or those infected for long periods of time (chronic infection). The concentration level of the biomarkers in a mammalian sample may demonstrate the infection status of the mammal. For example, a low concentration level of the biomarkers may indicate that the mammal is in a early stage of infection.

In one specific embodiment, a biomarker having at least one gene or a combination of at least two genes from the group consisting of gene sequences Q73SF4, Q73Y73, Q73ZE6, Q73SL7, Q73VK6, Q73XZ0, Q740D1 and Q73UE0 and expression products thereof may demonstrate the infection status of a mammal related to sigL-based vaccines. In another specific embodiment, a biomarker having at least one gene or a combination of at least two genes from the group consisting of gene sequences Q73VL6, Q73YW9, Q741L4, Q744E5, Q73YP5, Q73WE5, Q73U21, Q73UH9, Q741M5, Q742F4, and Q73 SU6 may demonstrate the infection status of a mammal related to sigH-based vaccines. In another embodiment, the present invention comprises host biomarkers listed in Table 3.

Further, the expression level of the biomarkers and/or specific combination of the biomarkers may allow early detection of mycobacterial infection. In one specific embodiment, the biomarkers may include at least one gene or a combination of at least two genes from the group consisting of gene sequences Q73SF4, Q73Y73, Q73ZE6, Q73SL7, Q73VK6, Q73XZ0, Q740D1 and Q73UE0 and expression products thereof. In another specific embodiment, the biomarkers may include at least one gene or a combination of at least two genes from the group consisting of gene sequences Q73VL6, Q73YW9, Q741L4, Q744E5, Q73YP5, Q73WE5, Q73U21, Q73UH9, Q741M5, Q742F4, and Q73SU6 and expression products thereof.

Applicants envision that the mycobacterial-specific biomarker may include genes or the polynucleotides containing less than an entire microbial or mammalian species genomes of the above genes. The biomarker of genes or the polynucleotides may be either single- or double-stranded nucleic acids. A polynucleotide may be RNA, DNA, cDNA, genomic DNA, chemically synthesized RNA or DNA or combinations thereof. The polynucleotides can be purified free of other components, such as proteins, lipids and other polynucleotides. For example, the polynucleotide may be 50%, 75%, 90%, 95%, 96%, 97%, 98%, 99%, or 100% purified. The purified polynucleotides may comprise additional heterologous nucleotides (i.e., nucleotides that are not from *mycobacterium*). The purified polynucleotides of the invention can also comprise other nucleotide sequences, such as sequences coding for linkers, primer, signal sequences, TMR stop transfer sequences, transmembrane domains, or ligands.

The gene or the polynucleotides of the invention may also comprise fragments that encode immunogenic polypeptides. Polynucleotides of the invention may encode full-length polypeptides, polypeptide fragments, and variant or fusion polypeptides. Polynucleotides of the invention may comprise coding sequences for naturally occurring polypeptides or may encode altered sequences that do not occur in nature. If desired, polynucleotides may be cloned into an expression vector comprising expression control elements, including for example, origins of replication, promoters, enhancers, or other regulatory elements that drive expression of the polynucleotides of the invention in host cells.

Differentiating *M. ap*-Infected Mammals from *M. bovis*-Infected Mammals

In another aspect, the present invention discloses a method for differentiating a *M. ap*-infected mammal from a *M. bovis*-infected mammal. The method comprises the steps of (a) obtaining a sample from the test mammal; (b) testing the sample for the concentration level of at least one of mycobacterial-specific markers and comparing the level of the markers with that detected in a *M. bovis* infected mammal; and (c) determining the status of the mammal.

In one embodiment, Applicants envision that the present invention may also be used in a skin test. For example, Applicants envision that a mammal may be inoculated with a reagent comprising any suitable antigen or a biomarker as discussed herein, and characteristic symptom of the mammal (e.g., skin induration, redness, size, and others) may be recorded. One can compare the characteristic symptom of the mammal with those in a standard (an infected mammal, non-infected mammal, *M. ap*-infected mammal or *M. bovis*-infected mammal) to determine the infection status of the mammal. Specifically, the present method may be used to differentiate infected from vaccinated animals.

In one embodiment, Applicants identify proteins or polypeptides as mycobacterial-specific markers for differentiating a *M. ap* infected mammal from a *M. bovis* infected mammal. Specifically, the mycobacterial-specific markers may comprise peptides conserved in *M. paratuberculosis* sequence but absent from *M. bovis*. Alternatively, the mycobacterial-specific markers may comprise peptides conserved in *M. bovis* sequence but absent from *M. paratuberculosis* sequence.

FIG. 1 demonstrates the alignment plot of amino acids deduced from the protein sequence in LipN of both *M. paratuberculosis* and *M. bovis*. In one embodiment, the biomarker comprises a protein or peptide sequence having at least 50%, 60%, 70%, 80%, 90%, 95% or 100% of the amino acid sequence of *M. paratuberculosis* which is not conserved in *M. bovis* (see the amino acid difference between *M. paratuberculosis* and *M. bovis* in FIG. 1) over a length of 2-100, 4-50, 6-30, and preferably 8-20 amino acids. In one embodiment, Applicants envision that a length of 8-20 amino acids that differentiate between *M. paratuberculosis* and *M. bovis*, as shown in FIG. 1, may be sufficient to differential between the infected of the two strains (*M. ap* and *M. bovis*).

In one embodiment, the concentration level of at least one of the mycobacterial-specific markers may be compared with that detected in a *M. bovis* infected mammal. For example, the presence (e.g., having a detectable concentration level) of the biomarkers specific for *M. paratuberculosis* shows the mammal may be *M. ap* infected. The concentration level as compared with a standard sample may also provide information regarding infection status such as early infection.

Detection of Biomarkers or Markers

The present biomarkers or markers may be detected by any suitable method. In one embodiment, the testing is via ELISA assay for antibodies formed against the biomarkers or markers.

The biomarker or marker in the present invention may be directly detected, e.g., by SELDI or MALDI-TOF. Alternatively, the biomarker may be detected directly or indirectly via interaction with a ligand or ligands such as an antibody or a biomarker-binding fragment thereof, or other peptide, or ligand, e.g. aptamer, or oligonucleotide, capable of specifically binding the biomarker. The ligand may possess a detectable label, such as a luminescent, fluorescent or radioactive label, and/or an affinity tag.

For example, detecting and/or quantifying may be performed by one or more method(s) selected from the group consisting of: SELDI (-TOF), MALDI (-TOF), a 1-D gel-based analysis, a 2-D gel-based analysis, Mass spectrometry (MS), reverse phase (RP) LC, size permeation (gel filtration), ion exchange, affinity, HPLC, UPLC and other LC or LC MS-based techniques. Appropriate LC MS techniques may include ICAT® (Applied Biosystems, CA, USA), or iTRAQ® (Applied Biosystems, CA, USA). Liquid chromatography (e.g., high pressure liquid chromatography (HPLC) or low pressure liquid chromatography (LPLC)), thin-layer chromatography, NMR (nuclear magnetic resonance) spectroscopy may also be used. Methods of diagnosing and/or monitoring according to the invention may comprise analyzing a plasma, serum or whole blood sample by a sandwich immunoassay to detect the presence or level of the biomarker. These methods are also suitable for clinical screening, prognosis, monitoring the results of therapy, identifying patients most likely to respond to a particular therapeutic treatment, for drug screening and development, and identification of new targets for drug treatment.

Detecting and/or quantifying the biomarkers or markers may be performed using an immunological method, involving an antibody, or a fragment thereof capable of specific binding to the biomarker. Suitable immunological methods include sandwich immunoassays, such as sandwich ELISA, in which the detection of the analyte biomarkers is performed using two antibodies which recognize different epitopes on a analyte biomarker; radioimmunoassays (RIA), direct, indirect or competitive enzyme linked immunosorbent assays (ELISA), enzyme immunoassays (EIA), Fluorescence immunoassays (FIA), western blotting, immunoprecipitation and any particle-based immunoassay (e.g., using gold, silver, or latex particles, magnetic particles, or Q-dots) Immunological methods may be performed, for example, in microtiter plate or strip format.

The gene or the polynucleotides of the invention may be detected by, for example, a probe or primer or a PCR primer. The gene or the polynucleotides of the invention may be the basis for designing a complimentary probe or primer, to detect the presence and/or quantity of *mycobacterium* in a subject, such as a biological sample. Probes are molecules capable of interacting with a target nucleic acid, typically in a sequence specific manner, for example, through hybridization. Primers are a subset of probes that can support an specific enzymatic manipulation and that can hybridize with a target nucleic acid such that the enzymatic manipulation occurs. A primer may be made from any combination of nucleotides or nucleotide derivatives or analogs available in the art that do not interfere with the enzymatic manipulation. "Specific" means that a gene sequence recognizes or matches another gene of the invention with greater affinity than to other non-specific molecules. Preferably, "specifically binds" or "specific to" also means a gene sequence recognizes and matches a gene sequence comprised in a wild-type *mycobacterium* or a *mycobacterium* mutant described herein, with greater affinity than to other non-specific molecules. More preferably, the probe or the primer is complimentary to a *mycobacterium* mutant with at least one mutation in the gene, e.g., sigH or sigL.

The hybridization of nucleic acids is well understood in the art. Typically a primer may be made from any combination of nucleotides or nucleotide derivatives or analogs available in the art. The ability of such primers to specifically hybridize to *mycobacterium* polynucleotide sequences will enable them to be of use in detecting the presence of complementary sequences in a given subject. The primers of the invention may hybridize to complementary sequences in a subject such as a biological sample, including, without limitation, saliva, sputum, blood, plasma, serum, urine, feces, cerebrospinal fluid, amniotic fluid, wound exudate, or tissue of the subject. Polynucleotides from the sample can be, for example, subjected to gel electrophoresis or other size separation techniques or can be immobilized without size separation.

The probes or the primers may also be labeled for the detection. Suitable labels, and methods for labeling primers are known in the art. For example, the label may include, without limitation, radioactive labels, biotin labels, fluorescent labels, chemiluminescent labels, bioluminescent labels, metal chelator labels and enzyme labels. The polynucleotides from the sample are contacted with the probes or primers under hybridization conditions of suitable stringencies. Preferably, the primer is fluorescent labeled. Also, the detection of the presence or quality of the gene sequence of interest can be accomplished by any method known in the art. For instance, the detection can be made by a DNA amplification reaction. In some embodiments, "amplification" of DNA denotes the use of polymerase chain reaction (PCR) to increase the concentration of a particular DNA sequence within a mixtures of DNA sequences.

In another embodiment, the amplification of DNA may be done by the loop-mediated isothermal amplification (LAMP). Similar to PCR, LAMP utilizes a polymerization-based reaction to amplify DNA from examined samples, but the enzyme for LAMP, Bst DNA polymerase large fragment, possesses a DNA strand displacement activity. This makes the DNA extension step possible without having to fully denature DNA templates. Moreover, the primers are designed in a way that a hairpin loop structure is formed in the first cycle of amplification, and the following products are further amplified in an auto-cycling manner. Therefore, in about an hour, the repeated reactions can amplify by $~10^9$ copies of DNA molecules and can be done at a constant temperature in a single heat block, instead of at various cycles of temperature in a relatively expensive thermal cycler. The detection of LAMP has been described in PCT patent application US2014/020248.

In one embodiment, the detection of the presence of the gene or the specific binding between the gene in *mycobacterium* mutant and a gene that is not a component of a subject's immune response to a particular vaccine may indicate a natural or experimental *mycobacterium* infection. For example, the absence of such binding or presence may indicate the absence of *mycobacterium* infection. Or, a second, separate gene, such as a mutated *mycobacterium* gene that is specific to a component of a mammal's immune response to a particular *mycobacterium* vaccine, may be used to detect corresponding antibodies produced in response to vaccination. Thus, if an antibody specific to a gene in *mycobacterium* vaccine is detected, then the mammal has been vaccinated and/or infected. The detection of neither genes indicates no infection and no vaccination. As such, various combinations can lead to a determination of the vaccination and/or infection status of the mammal.

Additional Markers

Table 3, which tabulates the result of one of the Examples drawn to host transcriptome analysis of goats, lists additional markers that will be useful for embodiments of the invention. The first part of Table 3 lists DNA markers that are useful for early diagnosis of John's disease in ruminants, as described above, because the markers differentiate infected from naive animals. The Table lists the locus in goats and provides homologous locus in cows, if it is known. Table 3 also lists host markers that can differentiate live attenuated vaccinated animals from naive animals and markers that can differentiate inactivated-vaccine immunized from naive animals.

Kits of the Present Invention

In another aspect, the present invention discloses a diagnostic kit suitable for carrying out the diagnostic method of the first aspect of the invention. In one embodiment, the kit may be a "one-day" kit, meaning that it is capable of providing the diagnostic result within one day of sample collection. In another embodiment, the kit may be able to provide a diagnostic result within 12, 10, 8, 6, 4, 2, 1 or 0.5 hours of sample collection.

In one embodiment, the diagnostic kit may be used for early detection of mycobacterial infection in a mammal. The diagnostic kit may also be used to differentiate a vaccinated mammal from an infected mammal. For infected mammals, the diagnostic kit may further be used to differentiated different pathogens such as *M. ap.* and *M. bovis.*

In one embodiment, the diagnostic kit may be portable. The portable diagnostic kit may specifically suitable for field testing. Applicants envision that the present diagnostic kit may be used in a farm field such as a milk farm, where farmers/veterinarians may collect samples and run the assay on the field (point of care assay) to identify early stages of Johne's disease infection and to differentiate infected from vaccinated mammals.

The kit may include a substrate. In one embodiment, the substrate may be coated with biomolecules such as antibodies, which are specifically binding to the specific biomarkers as discussed above. The biomolecules may further possess a detectable label, such as a luminescent, fluorescent or radioactive label, and/or an affinity tag.

In one embodiment of the present invention, the substrate may be used as a sample holder. Exemplary substrates may include microtiter strips or plates. In one specific embodiment, a sample such as a diluted serum may be pipetted into the wells of the microtiter plate or strip. A binding between the biomarkers in the serum and the biomolecules takes place. The presence or absence of the specific biomarkers or a combination of biomarkers as discussed above may indicate the infection status of the mammal.

The kit may further include a means of detection. The means of detection may include any detection method as discussed above. In one embodiment, the means of detection may be a spectroscopic technique, such as UV-Vis or MS. In one specific embodiment, the means of detection may be ELISA.

In one embodiment, the kit may include standard data for specific biomarker or a combination of biomarkers as discussed. One may compare the test result of a mammalian sample with the standard data for specific biomarker or a combination of biomarkers to determine the infection status of the mammal. For example, specific biomarkers or a combination of biomarkers may be visualized by a simple means of detection such as different colors. The detection result (e.g., showing one specific color) of a mammalian sample may be compared with the standard data (e.g., different colors for different biomarkers) to determine the infection status of the mammals.

In one embodiment, the kit may also be in the form of reagents (e.g. protein extract) that can be inoculated into animals to estimate the level of cell-mediate immunity (e.g. single intradermal comparative skin test, SICST). The reagents may include any of the biomarkers as discussed above. In one embodiment, the reagents may also include any genetically engineered vaccines. Suitable genetically engineered vaccines may include those Applicants previously proposed in PCT patent application US2014/02024.

The diagnostic kit may also include one or more of the following: instructions for use (detailing the method of the first aspect of the invention); sample collection apparatus (such as a needle and syringe); a chart for interpretation of the results; an electronic readout system; software providing a database for accurate data management.

The present invention has been described in terms of one or more preferred embodiments, and it should be appreciated that many equivalents, alternatives, variations, and modifications, aside from those expressly stated, are possible and within the scope of the invention.

EXAMPLES

Example 1

Proteomic Analysis of *M. avium* subsp. *paratuberculosis* Vaccine Candidates.

Johne's disease (JD) is a worldwide health problem for dairy herds that carries a heavy economic burden for producing safe food. Infected cattle suffer from chronic diarrhea, weight loss, low milk yield and low, but persistent mortality (1). For the dairy industry alone, the economic losses caused by JD are estimated to range between $200-$500 million annually, in the USA alone (2, 3). Identifying protective vaccine candidates against JD could be the cornerstone of controlling this widespread infection. In our group, we deciphered genomic information available for *M. ap* to identify key gene regulators that could control the expression of large number of genes. Throughout the genome of *M. ap* there are 19 sigma factors that act as global gene regulators that could contribute to the ability of *M. ap* to grow in many environments (4). Through previous funding from USDA, we examined several *M. ap* sigma (σ) factors that were important for growth in murine macrophages. Using transcriptional profiling, we compared mid-log phase *M. ap* to *M. ap* that had infected IFN-γ activated macrophages for 2 and 24 hours. Of the 19 sigma factors monitored, 6 sigma factor transcripts were up-regulated and one sigma factor transcript was down-regulated during the 24 hour time frame. Of the up-regulated transcripts, the sigL transcript was the only transcript up-regulated 2 hours after infection while sigH was up-regulated at 24 hrs (5). SigL is implicated in cell membrane protein biosynthesis as well as virulence in *M. tuberculosis* (6) while SigH was shown to be involved in combating the host intracellular responses such as oxidative stress (7).

To assess the role of sigL and sigH in *M. ap* virulence, we replaced the target sigma factors gene coding regions with a hygromycin-resistant gene cassette in *M. ap* K-10 using a specialized transduction protocol that was adapted for *M. ap*. Both genes were shown to be necessary for *M. ap* virulence in different stages of murine infection as detailed before (5, 8). Interestingly, the same mutants were shown to provide protective immunity against challenge with the virulent strain of *M. ap* when they were used as vaccine candidates in mice. To better analyze proteins expressed in each mutant, we grow cultures of *M. ap*ΔsigL, *M. ap*ΔsigH mutants and the wild type parent strain, *M. ap* K10 to mid-log phase. All cultures were washed twice in PBS, resuspended in buffer cocktail with endonuclease before proteomic analysis using nano-Liquid Chromatography-Mass Spectroscopy-MS (nano-LC MS/MS) at the University of Wisconsin Biotechnology Center. From 3 biological replicates, a total of ~900 proteins were identified in this analysis comparing sigL and sigH mutant to *M. ap* K10 proteome.

Diagnostic Markers for JD-Vaccinated Animals.

A major problem in employing mass vaccination program for the control of JD in dairy herds is the inability to differentiate between infected and vaccinated animals with the current vaccine (DIVA principal). In addition, vaccinated animals could not be differentiated from positive reaction to the infection with *M. bovis*, a significant health problem for domesticated and wildlife animals. However, the DIVA principal and ability to distinguish between *M. bovis* and JD vaccinated animals could be achieved in genetically engineered vaccines (such as live attenuated vaccines based on sigL and sigH mutant) using a novel approach designed by the Applicant. In this approach, a simple blood test targeting proteins or sequences present in *M. ap* wild type strain and with lower expression level in the vaccine strain or even not encoded in the *M. bovis* genome would be developed. The target proteins include the following list of genes that could be used for the sigL-based vaccines.

TABLE 1

*M. ap* proteins that are significantly over-expressed in the wild type strain and not in the sigL-vaccine and could be used for sigL-DIVA testing.

| Number | Accession Number | Fold Change (K10/sigH) | Name/Function |
| --- | --- | --- | --- |
| 1 | Q73SF4 | 1.75 | hypothetical protein |
| 2 | Q73Y73 | 2.66 | aldehyde dehydrogenase (NAD+) |
| 3 | Q73ZE6 | 2.13 | nucleotide-sugar epimerase EpiA |
| 4 | Q73SL7 | 2.69 | hypothetical protein Mb0574c |
| 5 | Q73VK6 | 1.14 | oxidoreductase |
| 6 | Q73XZ0 | 1.88 | antigen CFP2 |
| 7 | Q740D1 | 4.71 | peptide synthetase Nrp |
| 8 | Q73UE0 | 1.99 | cutinase |

TABLE 2

*M. ap* proteins that are significantly over-expressed in the wild type strain and not in the sigH-vaccine and could be used for sigH-DIVA testing.

| Number | Accession Number | Fold Change (WT/sigH) | Name/Function |
| --- | --- | --- | --- |
| 1 | Q73VL6 | 3.05 | diguanylate cyclase (GGDEF) domain-containing protein |
| 2 | Q73YW9 | 1.64 | PE family protein, partial |
| 3 | Q741L4 | 1.88 | hypothetical protein |
| 4 | Q744E5 | 2.67 | ABC transporter ATPase |
| 5 | Q73YP5 | 2.47 | Pup--protein ligase |
| 6 | Q73WE5 | 1.78 | arginine decarboxylase |
| 7 | Q73U21 | 1.88 | PE family protein PE17 |
| 8 | Q73UH9 | 2.16 | XRE family transcriptional regulator |
| 9 | Q741M5 | 2.11 | nitroreductase |
| 10 | Q742F4 | 2.72 | metallo-beta-lactamase |
| 11 | Q73SU6 | 2.47 | 3-ketoacyl-ACP reductase |

In addition, another vaccine candidate is based on lipN mutant. In this case, epitopes that are different in the *M. ap* protein compared to those in *M. bovis* will be the target for DIVA diagnostic test.

FIG. 1 shows the alignment plot of amino acids deduced from the protein sequence in LipN of both *M. paratuberculosis* and *M. bovis*. Peptides conserved in *M. paratuberculosis* sequence but absent from *M. bovis* would be the target for developing the DIVA test.

Example 2—Prophetic Example

Objective: Develop Simple Assays to Differentiate Infected and Vaccinated Animals (DIVA).

Taking advantage of the defined genetic mutation introduced in the current vaccine candidates, we will develop a multiplex PCR-based assay to differentiate *M. ap*-infected from LAV-vaccinated animals. In addition, we will prepare whole cell lysates (WCL) from our LAV constructs to be used for single intradermal comparative skin test (SICST) to differentiate *M. bovis*-infected from LAV-vaccinated animals.

Development of an efficient, safe and commercially viable vaccine against chronic infections is ordinarily arduous and prolonged. We have already identified promising candidates that could significantly reduce *M. ap* infection in 2 different animal models. The long-term goal is to develop these candidates into an easily administered, highly effective vaccine to control JD in dairy operations. Our novel application of adjuvant-supplemented LAV to create effective JD vaccines and the development of sensitive DIVA assays will further improve our chances to commercialize this targeted vaccine.

Rationale.

An important hurdle in the use of a live attenuated vaccine (LAV) to control JD is the ability to distinguish between vaccinated and infected animals. Infection with a wild type strain of *M. ap* or *M. bovis* will interfere with the current standard tests for JD (PCR or ELISA) and for bovine tuberculosis (intradermal skin test). To overcome such hurdles, we designed a multiplex PCR-based assay using unique sequences present in our LAV which will provide a simple, cost-effective assay to determine if an animal has been vaccinated or is infected with virulent *M. ap*. This assay will take advantage of the reliability and speed of amplification-based assays. To differentiate *M. bovis*-infected animals form LAV-vaccinated animals, we will utilize the whole cell lysates prepared from the LAV candidates to conduct a single intradermal comparative skin test (SICST). We hypothesize that significant difference in the antigenic composition of both LAV and *M. bovis* will allow us to develop a CMI-based assay. Our proteomic analysis provided us with an example of how the proteome of LAV construct can be highly different from the wild type or *M. bovis* strains, even when a relatively small number of proteins were analyzed. In the proposed SICST, both *M. bovis* PPD and LAV-WCL will be inoculated to the same side of animal's neck to compare the degree of induration for each preparation. A similar test using *M. avium* sensitin is already in use in several parts of the world (Daniel et al., 2009; Gey van Pittius et al., 2012) where infection with the opportunistic *M. avium* is prevalent and need to be differentiated from infection with *M. bovis*. In our hands, goats immunized with LAV showed higher responses to *M. ap* PPD compared to *M. bovis*. Also, experimentally, we were able to show that PBMC cells stimulated with *M. ap* whole cell lysate outperformed the *M. ap* PPD in the standard IFN-γ release assay. Accordingly, in this part of the project, we will use WCL from LAV instead of PPD, which could be missing key stimulatory antigens.

Experimental Design.

Figure 2B:
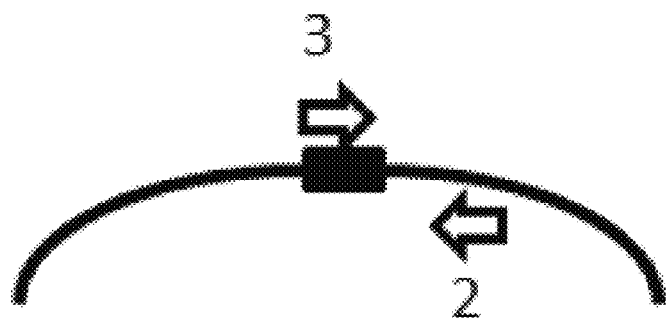
FIG. 2B is a diagram showing multiplex PCR strategy using 3 primers, specifically, LAV strain with scar sequence from hygromycin cassette removal represented by the black rectangle.

Development of a DIVA using PCR. Our mutant strains are generated using a previously reported method in which the target gene is replaced with a hygromycin-resistance cassette, which is then subsequently removed, leaving only a "scar" sequence in its place. Since this sequence is unique to our mutant strain, we can detect its presence using PCR. This PCR will be performed in multiplex with a second product amplified that consists of the original gene that was deleted in our vaccine strain (FIG. 2). Thus, a single PCR reaction with 3 primers will provide a positive result for both vaccinated animals and infected animals, with the ability to differentiate them based on the size of the PCR product. This assay will be validated using fecal samples spiked with known quantities of both virulent and LAV strains of *M. ap*. The amplification target for this PCR will include fecal or saliva samples collected from suspected animals, similar to the sampling strategy we used before for assaying vaccine safety (preliminary results).

Evaluate the PCR assay using goat samples. Using fecal samples collected from goats in Objective II (above), we will validate the DIVA assay by extracting DNA from fecal samples and subjecting it to our assay. The PBS-vaccinated group will serve as a control for detecting only the challenge strain. Validation of the developed test will be further evaluated on with samples collected from infected and vaccinated cows in Phase II of this project.

Development of SICST. We will prepare whole cell lysate from early, mid and stationary phase cultures of our LAV candidates using standard protocols (Al-Khodari et al., 2011; Xi et al., 2011). At 1 month post immunization or 4 months post challenge (different times from regular testing with Johnin), goats used for experiments in Objective II will be inoculated with 0.1 ml (100 µg) of Tuberculin PPD or LAV-WCL. At 72 hrs post inoculation, skin indurations will be measured using a digital caliper. Skin induration measurements will be compiled from all animals and compared between groups. To start test interpretation, we can get guidance from similar tests performed on M. bovis infected animals (Bezos et al., 2010; Daniel et al., 2009). Any induration >5 mm of the WCL above the induration of the Tuberculin will be considered positive for LAV immunization while the vice versa will be an indication of infection with M. bovis. To standardize the last part of this test interpretation, we will have to have access to M. bovis infected goats. This part of the project will be performed as part of the test validation in Phase II of the project.

Expected results and alternative approaches. Data generated from experiments proposed here will develop easy to perform assays to distinguish vaccinated from M. ap or M. bovis-infected animals. One potential issue with the PCR-based assay is the requirement that the animal is shedding bacteria or that bacterial DNA is present in the feces. Since bacterial shedding in Johne's disease is intermittent, this assay may not always be able to detect DNA from either strain. If this approach does not meet the needs of Johne's disease prevention programs, we will develop an ELISA-based assay. Since our LAV strains lack 1 or more proteins due to deletion of the lipN and fabG2_2 genes, we could develop an ELISA against these proteins.

In another embodiment of the invention, we will utilize proteomic data on pgsN and/or pgsF to deduce new targets.

Finally, in another embodiment of the invention, the SICST might not be sensitive to respond differentially to antigens from LAV or M. bovis infection in some situations. In this case, we could increase the concentration of the used antigens or use cytokine profiles associated with vaccinated animals as the DIVA assay. In this case, the test would be completely evaluated in Phase II of this project when we can include M. bovis infected animals for comparative analysis.

Example 3—Biomarkers for Early Diagnosis and Differentiation of Mycobacterial Infections Johne's disease, caused by *Mycobacterium avium* subspecies *paratuberculosis* (MAP) is a chronic gastroenteritis of ruminants. Although infection often occurs within the first few months of life, clinical signs do not appear until 2-5 years of age. Current diagnostic tests, such as fecal culture and ELISA, have poor sensitivity for detection of the sub-clinical phase of disease. Therefore, biomarkers have been increasingly investigated as a method for sub-clinical detection.

In this project, we set out to develop rapid assays (e.g. PCR or field skin test) for early detection of presence of Johne's disease and for the differentiation of Johne's disease vaccinated vs. infected animals (with MAP or *M. bovis*). To speed up the project outcome, we capitalized on ongoing vaccine study in goats (*Capra hircus*) and collected Peripheral blood mononuclear cells (PBMC's) for transcriptional profiling followed by gene prediction for disease initiation and progression.

The PBMC's have been shown to be a predictor of infection and inflammatory disease. The PBMC transcriptomes of the goats were profiled using RNA-sequencing (RNA-Seq) to evaluate differential gene expression between a subset of samples from either 30 days post-vaccination, 30 days post-infection, or a naive, non-infected control group (3-4 biological replicates per group). Preliminary results on differential gene expression indicated the presence of 88 significantly differentially expressed genes out of 11,009 genes between goats at 30 days post-infection and the naïve, non-infected controls. The 30 days post-vaccination group had 720 out of 10,985 and 746 out of 11,099 significantly differentially expressed genes compared to the naïve, non-infected control group and the 30 days post-infection group, respectively. However, preliminary evaluation of the expressed genes indicated a large number of genes with immunological and inflammatory functions, including IL-18 binding protein, IFN-γ, IL-17A, and IL-22. As a result of this inquiry, Table 3 summarizes selected genes/targets suitable to use in the present invention.

TABLE 3

List of DNA markers that are derived from the host transcriptome analysis and can be used for early diagnosis of Johne's disease in ruminants (e.g., cattle, goats, sheep and camels).

| Locus in goats | Symbol | Protein | Description | Homolog in Bos taurus (cows) | Homolog description |
|---|---|---|---|---|---|
| Selected list of host (goat and cow) markers that can differentiate infected from naïve animals. The loci of the up-regulated biomarkers in infected animals are underlined and bolded. | | | | | |
| NW_005125111.1: 0-184 | unplaced genomic scaffold | N/A | N/A | | |
| NW_005101181.1: 1703-1858 | unplaced genomic scaffold | N/A | N/A | | |
| NW_005101181.1: 168292-168418 | LOC102180841 | XP_005701370.1 | PREDICTED: multidrug resistance-associated protein 4-like | XP_005199610 | multidrug resistance-associated protein 4-like isoform X1 |

TABLE 3-continued

List of DNA markers that are derived from the host transcriptome
analysis and can be used for early diagnosis of Johne's disease
in ruminants (e.g., cattle, goats, sheep and camels).

| Locus in goats | Symbol | Protein | Description | Homolog in Bos taurus (cows) | Homolog description |
|---|---|---|---|---|---|
| NC_022320.1: 39973839-39974080 | Non-coding region | N/A | N/A | | |
| NC_022297.1: 44037534-44043184 | IL-22 | XP_005680263.1 | interleukin 22 | NP_001091849.1 | interleukin 22 |
| NC_022296.1: 81262820-81263390 | Non-coding region | N/A | N/A | | |
| NW_005101844.1: 141791-142987 | ABCC4 | XP_005701761.1 | PREDICTED: multidrug resistance-associated protein 4-like, partial | XP_010820300.1 | PREDICTED: multidrug resistance-associated protein 4 isoform X1 |
| NW_005101711.1: 48628-48757 | LOC102185556 | XP_005701708.1 | PREDICTED: multidrug resistance-associated protein 4-like | XP_003585348.3 | PREDICTED: multidrug resistance-associated protein 4 isoform X1 |
| NW_005132660.1: 0-240 | unplaced genomic scaffold | N/A | N/A | | |
| NW_005109943.1: 2-224 | unplaced genomic scaffold | N/A | N/A | | |
| NW_005149706.1: 0-366 | unplaced genomic scaffold | N/A | N/A | | |
| NW_005153011.1: 2-407 | unplaced genomic scaffold | N/A | N/A | | |

Selected list of host (goat and cow) markers that can differentiate Live attenuated vaccinated (LAV) from naïve animals. The loci of the up-regulated biomarkers in vaccinated animals with live-attenuated vaccines are underlined and bolded.

| Locus in goats | Symbol | Protein | Description | Homolog in Bos taurus (cows) | Homolog description |
|---|---|---|---|---|---|
| NC_022296.1: 32351255-32351413 | Non-coding region | N/A | N/A | | |
| NC_022307.1: 44045143-44403012 | Non-coding region | N/A | N/A | | |
| NC_022295.1: 13176472-13182094 | Non-coding region | N/A | N/A | | |
| NC_022321.1: 6000551-6000875 | Non-coding region | N/A | N/A | | |
| NW_005126018.1: 16-203 | unplaced genomic scaffold | N/A | N/A | | |
| NW_005101711.1: 48628-48757 | LOC102185556 | XP_005701708.1 | PREDICTED: multidrug resistance-associated protein 4-like | XP_003585348.3 | PREDICTED: multidrug resistance-associated protein 4 isoform X1 |
| NW_005101844.1: 141790-142987 | ABCC4 | XP_005701761.1 | PREDICTED: multidrug resistance-associated protein 4-like, partial | XP_010820300.1 | PREDICTED: multidrug resistance-associated protein 4 isoform X1 |
| NW_005101645.1: 16151-23647 | unplaced genomic scaffold | N/A | N/A | | |

Selected list of host (goat and cow) markers that can differentiate inactivated-vaccine immunized from naïve animals. The loci of the up-regulated biomarkers in vaccinated animals with inactivated vaccines are underlined and bolded.

| Locus in goats | Symbol | Protein | Description | Homolog in Bos taurus (cows) | Homolog description |
|---|---|---|---|---|---|
| NW_005125111.1: 0-184 | unplaced genomic scaffold | N/A | N/A | | |
| NC_022320.1: 39973839-39974080 | Non-coding region | N/A | N/A | | |
| NC_022303.1: 46207878-46237242 | Non-coding region | N/A | N/A | | |

TABLE 3-continued

List of DNA markers that are derived from the host transcriptome analysis and can be used for early diagnosis of Johne's disease in ruminants (e.g., cattle, goats, sheep and camels).

| Locus in goats | Symbol | Protein | Description | Homolog in Bos taurus (cows) | Homolog description |
|---|---|---|---|---|---|
| NC_022296.1: 81262820-81263390 | Non-coding region | N/A | N/A | | |
| NW_005101711.1: 48628-48757 | LOC102185556 | XP_005701708.1 | PREDICTED: multidrug resistance-associated protein 4-like | XP_003585348.3 | PREDICTED: multidrug resistance-associated protein 4 isoform X1 |
| NW_005102056.1: 2049-9786 | LOC102190036 | XP_005701827.1 | PREDICTED: tyrosine-protein phosphatase non-receptor type substrate 1-like, partial | NP_786982.1 | tyrosine-protein phosphatase non-receptor type substrate 1 precursor |
| NC_022309.1: 40520580-40588889 | — | XP_005691363.1 | PREDICTED: protein FAM198B | NP_001077247.1 | protein FAM198B |
| NW_005101931.1: 48185-54192 | LOC102180487 | XP_005701808.1 | PREDICTED: interferon alpha-inducible protein 27-like protein 2-like | NP_001069925.2 | uncharacterized protein LOC617420 |
| NW_005164924.1: 1-636 | unplaced genomic scaffold | N/A | N/A | | |

REFERENCES

1. Collins M T, Sockett D C, Goodger W J, Conrad T A, Thomas C B, Carr D J. 1994. Herd prevalence and geographic distribution of, and risk factors for, bovine paratuberculosis in Wisconsin. J Am Vet Med Assoc 204:636-641.
2. Linnabary R D, Meerdink G L, Collins M T, Stabel J R, Sweeney R W, Washington M K, Wells S J. 2001. Johne's disease in Cattle. Council for Agricultural Science and Technology 17:1-10.
3. Losinger W C. 2005. Economic impact of reduced milk production associated with Johne's disease on dairy operations in the USA. J. Dairy Res. 72:425-432.
4. Li L, Bannantine J P, Zhang Q, Amonsin A, May B J, Alt D, Banerji N, Kanjilal S, Kapur V. 2005. The complete genome sequence of Mycobacterium avium subspecies paratuberculosis. Proceedings of the National Academy of Sciences of the United States of America 102:12344-12349.
5. Ghosh P, Wu C-w, Talaat A M. 2013. Key Role for the Alternative Sigma Factor, SigH, in the Intracellular Life of Mycobacterium avium subsp. paratuberculosis during Macrophage Stress. Infect. Immun 81:2242-2257.
6. Hahn M Y, Raman S, Anaya M, Husson R N. 2005. The mycobacterium tuberculosis extracytoplasmic-function sigma factor SigL regulates polyketide synthases and secreted or membrane proteins and is required for virulence. Journal of Bacteriology. 187:7062-7071.
7. Park S T, Kang C M, Husson R N. 2008. Regulation of the SigH stress response regulon by an essential protein kinase in Mycobacterium tuberculosis. Proceedings of the National Academy of Sciences U.S.A. 105:13105-13110.
8. Ghosh P, Steinberg H, Talaat A M. 2014. Virulence and Immunity Orchestrated by the Global Gene Regulator sigL in Mycobacterium avium subsp. paratuberculosis. Infect Immun 82:3066-3075.
9. Al-Khodari, N. Y., Al-Attiyah, R. & Mustafa, A. S. (2011). Identification, Diagnostic Potential, and Natural Expression of Immunodominant Seroreactive Peptides Encoded by Five Mycobacterium tuberculosis-Specific Genomic Regions. Clinical and Vaccine Immunology 18, 477-482.
10. Bezos, J., de Juan, L., Romero, B., Alvarez, J., Mazzucchelli, F., Mateos, A., Dominguez, L. & Aranaz, A. (2010). Experimental infection with Mycobacterium caprae in goats and evaluation of immunological status in tuberculosis and paratuberculosis co-infected animals. Veterinary Immunology and Immunopathology 133, 269-275.
11. Daniel, R., Evans, H., Rolfe, S., Rua-Domenech, R., Crawshaw, T., Higgins, R. J., Schock, A. & Clifton-Hadley, R. (2009). Outbreak of tuberculosis caused by Mycobacterium bovis in golden Guernsey goats in Great Britain. Vet rec %19; 165, 335-342.
12. Gey van Pittius, N. C., Perrett, K. D., Michel, A. L., Keet, D. F., Hlokwe, T., Streicher, E. M., Warren, R. M. & van Heiden, P. D. (2012). Infection of African Buffalo (Syncerus Caffer) by Oryx Bacillus, A Rare Member of the Antelope Clade of the Mycobacterium Tuberculosis Complex. Journal of Wildlife Diseases 48, 849-857.
Xi, X., Zhang, X., Wang, B. & other authors (2011). A novel strategy to screen Bacillus Calmette-Guerin protein antigen recognized by gammadelta TCR. PLoS ONE 6, e18809.

I claim:

1. A method for diagnosis of mycobacterial infection in a mammal, the method comprising the steps of
   a) obtaining a sample from the mammal, wherein the sample is of a first type;
   b) testing the sample for the concentration level of at least one mycobacterial-specific biomarker selected from the group consisting of Q73SF4, Q73Y73, Q73ZE6, Q73SL7, Q73VK6, Q73XZ0, Q740D1, Q73UE0, Q73VL6, Q73YW9, Q741L4, Q744E5, Q73YP5, Q73WE5, Q73U21, Q73UH9, Q741M5, Q742F4, Q73SU6, and antibodies specific thereto and comparing the level of the mycobacterial-specific biomarker against the level detected in an uninfected mammalian sample, wherein the uninfected mammalian sample is of the first type and is from the same species of mammal; and
   c) determining the infection status of the mammal, wherein an increase in the concentration level of the mycobacterial-specific biomarker is indicative of a mycobacterial infection in the mammal.

2. The method of claim 1, wherein the method is used for early diagnosis and detection of mycobacterial infection in a mammal.

3. The method of claim 1, wherein the mycobacterial-specific biomarker is an antibody and the testing is via ELISA assay.

4. The method of claim 1, wherein the sample is a blood sample.

5. The method of claim 1, wherein the mammal is selected from the group consisting of bubaline, elephantine, musteline, pardine, phocine, rhinocerine, caprine, hircine, leonine, leporine, lupine, lyncine, murine, rusine, tigrine, ursine, vulpine, zebrine, vespertilionine, porcine, bovine, equine, swine, elaphine, ovine, caprine, camelidae, feline, cervine, primate, human and canine mammals.

6. The method of claim 1 wherein the mammal is selected from the group of pig, cow, human, rodent, sheep, goat and deer.

7. The method of claim 1, wherein the mammal is selected from the group consisting of cow, sheep and goat.

8. The method of claim 1, wherein the mammal is a cow.

9. The method of claim 1, wherein the mycobacterial-specific biomarker comprises at least one member selected from the group consisting of Q73SF4, Q73Y73, Q73ZE6, Q73SL7, Q73VK6, Q73XZ0, Q740D1 and Q73UE0.

10. The method of claim 1, wherein the mycobacterial-specific biomarker comprises at least one member selected from the group consisting of Q73VL6, Q73YW9, Q741L4, Q744E5, Q73YP5, Q73WE5, Q73U21, Q73UH9, Q741M5, Q742F4, and Q73 SU6.

* * * * *

UNITED STATES PATENT AND TRADEMARK OFFICE
CERTIFICATE OF CORRECTION

PATENT NO. : 10,054,586 B2
APPLICATION NO. : 14/923478
DATED : August 21, 2018
INVENTOR(S) : Adel M. Talaat Page 1 of 1

It is certified that error appears in the above-identified patent and that said Letters Patent is hereby corrected as shown below:

In the Specification

Column 22, Line 60, "Heiden" should be --Helden--.

Signed and Sealed this
Thirteenth Day of November, 2018

Andrei Iancu
*Director of the United States Patent and Trademark Office*

SEQUENCE LISTING

<160> NUMBER OF SEQ ID NOS: 3

<210> SEQ ID NO 1
<211> LENGTH: 376
<212> TYPE: PRT
<213> ORGANISM: Mycobacterium bovis

<400> SEQUENCE: 1

```
Met Thr Lys Ser Leu Pro Gly Val Ala Asp Leu Arg Leu Gly Ala Asn
1               5                   10                  15

His Pro Arg Met Trp Thr Arg Arg Val Gln Gly Thr Val Val Asn Val
            20                  25                  30

Gly Val Lys Val Leu Pro Trp Ile Pro Thr Pro Ala Lys Arg Ile Leu
        35                  40                  45

Ser Ala Gly Arg Ser Val Ile Ile Asp Gly Asn Thr Leu Asp Pro Thr
    50                  55                  60

Leu Gln Leu Met Leu Ser Thr Ser Arg Ile Phe Gly Val Asp Gly Leu
65                  70                  75                  80

Ala Val Asp Asp Asp Ile Val Ala Ser Arg Ala His Met Arg Ala Ile
                85                  90                  95

Cys Glu Ala Met Pro Gly Pro Gln Ile His Val Asp Val Thr Asp Leu
            100                 105                 110

Ser Ile Pro Gly Pro Ala Gly Glu Ile Pro Ala Arg His Tyr Arg Pro
        115                 120                 125

Ser Gly Gly Gly Ala Thr Pro Leu Leu Val Phe Tyr His Gly Gly Gly
    130                 135                 140

Trp Thr Leu Gly Asp Leu Asp Thr His Asp Ala Leu Cys Arg Leu Thr
145                 150                 155                 160

Cys Arg Asp Ala Asp Ile Gln Val Leu Ser Ile Asp Tyr Arg Leu Ala
                165                 170                 175

Pro Glu His Pro Ala Pro Ala Ala Val Glu Asp Ala Tyr Ala Ala Phe
            180                 185                 190

Val Trp Ala His Glu His Ala Ser Asp Glu Phe Gly Ala Leu Pro Gly
        195                 200                 205

Arg Val Ala Val Gly Gly Asp Ser Ala Gly Gly Asn Leu Ser Ala Val
    210                 215                 220

Val Cys Gln Leu Ala Arg Asp Lys Ala Arg Tyr Glu Gly Gly Pro Thr
225                 230                 235                 240

Pro Val Leu Gln Trp Leu Leu Tyr Pro Arg Thr Asp Phe Thr Ala Gln
                245                 250                 255

Thr Arg Ser Met Gly Leu Phe Gly Asn Gly Phe Leu Leu Thr Lys Arg
            260                 265                 270

Asp Ile Asp Trp Phe His Thr Gln Tyr Leu Arg Asp Ser Asp Val Asp
        275                 280                 285

Pro Ala Asp Pro Arg Leu Ser Pro Leu Leu Ala Glu Ser Leu Ser Gly
    290                 295                 300

Leu Ala Pro Ala Leu Ile Ala Val Ala Gly Phe Asp Pro Leu Arg Asp
305                 310                 315                 320

Glu Gly Glu Ser Tyr Ala Lys Ala Leu Arg Ala Ala Gly Thr Ala Val
                325                 330                 335

Asp Leu Arg Tyr Leu Gly Ser Leu Thr His Gly Phe Leu Asn Leu Phe
            340                 345                 350

Gln Leu Gly Gly Gly Ser Ala Ala Gly Thr Asn Glu Leu Ile Ser Ala
        355                 360                 365
```

Leu Arg Ala His Leu Ser Arg Val
    370                 375

<210> SEQ ID NO 2
<211> LENGTH: 373
<212> TYPE: PRT
<213> ORGANISM: Mycobacterium paratuberculosis

<400> SEQUENCE: 2

Met Thr Lys Pro Leu Thr Asp Thr Ala Pro Val Asp Pro Gly Ala Gln
1               5                   10                  15

Arg Gly Ser Met Pro Leu Thr Asn Arg Ile Gln Gly Ala Val Thr Ser
            20                  25                  30

Val Gly Val Lys Val Ile Pro Trp Ile Pro Thr Ala Val Arg Arg Gly
        35                  40                  45

Leu Val Arg Gly Arg Ser Val Ile Ile Asp Gly Asn Thr Leu Asp Pro
    50                  55                  60

Thr Leu Gln Leu Met Leu Ser Gly Leu Arg Ala Val Gly Ile Asp Gly
65                  70                  75                  80

Leu Val Val Asp Asp Asp Pro Glu Leu Ser Arg Ala Gln Met His Glu
                85                  90                  95

Ser Thr Val Gly Phe Pro Gly Pro Gln Ile His Val Asp Val Ala Glu
            100                 105                 110

Leu Ala Leu Pro Gly Pro Ala Gly Asp Ile Pro Ala Arg His Tyr Arg
        115                 120                 125

Pro Ala Gly Gly Glu Thr Gln Ala Pro Leu Leu Val Phe Tyr His Gly
    130                 135                 140

Gly Gly Trp Ser Ile Gly Asp Leu Asp Thr His Asp Ser Leu Cys Arg
145                 150                 155                 160

Leu Thr Cys Arg Asp Ala Gly Ile His Val Leu Ser Ile Asp Tyr Arg
                165                 170                 175

Leu Ala Pro Glu His Pro Ala Pro Ala Ala Ile Asp Asp Ala Tyr Ala
            180                 185                 190

Ala Phe Thr Trp Ala His Glu His Ala Gly Glu Leu Gly Ala Ile Pro
        195                 200                 205

Gly Arg Val Ala Val Gly Gly Asp Ser Ala Gly Gly Asn Leu Ala Ala
    210                 215                 220

Val Val Ser Gln Leu Ala Arg Asp Ala Gly Gly Pro Ala Pro Val Leu
225                 230                 235                 240

Gln Trp Leu Ile Tyr Pro Arg Thr Asp Phe Thr Ala Arg Thr Arg Ser
                245                 250                 255

Leu Ser Leu Phe Ser Arg Gly Phe Leu Leu Thr Lys Arg Asp Ile Asp
            260                 265                 270

Trp Phe Glu Ser Gln Tyr Leu Arg Asn Ser Arg Leu Asp Arg Thr Asp
        275                 280                 285

Pro Arg Val Ser Pro Ala Leu Ala Glu Ser Leu Ala Gly Leu Ala Pro
    290                 295                 300

Ala Leu Ile Ala Val Ala Gly Phe Asp Pro Leu Arg Asp Glu Gly Gln
305                 310                 315                 320

Ser Tyr Ala Glu Ala Leu Arg Ala Ala Gly Thr Pro Val Asp Leu Arg
                325                 330                 335

Tyr Leu Gly Ser Leu Thr His Gly Phe Ala Asn Leu Phe Gln Leu Gly
            340                 345                 350

Gly Asp Ser Met Val Ala Thr Ser Glu Leu Ile Ser Ala Leu Arg Ala
        355                 360                 365

His Leu Ser Arg Val
    370

<210> SEQ ID NO 3
<211> LENGTH: 378
<212> TYPE: PRT
<213> ORGANISM: Artificial Sequence
<220> FEATURE:
<223> OTHER INFORMATION: Analytical Consensus Seqeunce
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (10)..(13)
<223> OTHER INFORMATION: Xaa can be any naturally occurring amino acid
<220> FEATURE:
<221> NAME/KEY: misc_feature
<222> LOCATION: (16)..(19)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (44)..(46)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(51)
<223> OTHER INFORMATION: Xaa can be any naturally occurring amino acid
<220> FEATURE:
<221> NAME/KEY: misc_feature
<222> LOCATION: (72)..(73)
<223> OTHER INFORMATION: Xaa can be any naturally occurring amino acid
<220> FEATURE:
<221> NAME/KEY: misc_feature
<222> LOCATION: (75)..(76)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid

```
<220> FEATURE:
<221> NAME/KEY: misc_feature
<222> LOCATION: (87)..(89)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(101)
<223> OTHER INFORMATION: Xaa can be any naturally occurring amino acid
<220> FEATURE:
<221> NAME/KEY: misc_feature
<222> LOCATION: (111)..(112)
<223> OTHER INFORMATION: Xaa can be any naturally occurring amino acid
<220> FEATURE:
<221> NAME/KEY: misc_feature
<222> LOCATION: (114)..(115)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (133)..(134)
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (148)..(149)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (169)..(169)
<223> OTHER INFORMATION: Xaa can be any naturally occurring amino acid
<220> FEATURE:
<221> NAME/KEY: misc_feature
<222> LOCATION: (187)..(188)
<223> OTHER INFORMATION: Xaa can be any naturally occurring amino acid
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (205)..(205)
<223> OTHER INFORMATION: Xaa can be any naturally occurring amino acid
<220> FEATURE:
<221> NAME/KEY: misc_feature
<222> LOCATION: (208)..(208)
<223> OTHER INFORMATION: Xaa can be any naturally occurring amino acid
<220> FEATURE:
<221> NAME/KEY: misc_feature
<222> LOCATION: (224)..(224)
<223> OTHER INFORMATION: Xaa can be any naturally occurring amino acid
<220> FEATURE:
<221> NAME/KEY: misc_feature
<222> LOCATION: (228)..(228)
```

```
<223> OTHER INFORMATION: Xaa can be any naturally occurring amino acid
<220> FEATURE:
<221> NAME/KEY: misc_feature
<222> LOCATION: (234)..(234)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (258)..(258)
<223> OTHER INFORMATION: Xaa can be any naturally occurring amino acid
<220> FEATURE:
<221> NAME/KEY: misc_feature
<222> LOCATION: (262)..(263)
<223> OTHER INFORMATION: Xaa can be any naturally occurring amino acid
<220> FEATURE:
<221> NAME/KEY: misc_feature
<222> LOCATION: (266)..(267)
<223> OTHER INFORMATION: Xaa can be any naturally occurring amino acid
<220> FEATURE:
<221> NAME/KEY: misc_feature
<222> LOCATION: (280)..(281)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (288)..(289)
<223> OTHER INFORMATION: Xaa can be any naturally occurring amino acid
<220> FEATURE:
<221> NAME/KEY: misc_feature
<222> LOCATION: (291)..(292)
<223> OTHER INFORMATION: Xaa can be any naturally occurring amino acid
<220> FEATURE:
<221> NAME/KEY: misc_feature
<222> LOCATION: (296)..(296)
<223> OTHER INFORMATION: Xaa can be any naturally occurring amino acid
<220> FEATURE:
<221> NAME/KEY: misc_feature
<222> LOCATION: (299)..(299)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (325)..(325)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (337)..(337)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid
<220> FEATURE:
<221> NAME/KEY: misc_feature
<222> LOCATION: (359)..(359)
<223> OTHER INFORMATION: Xaa can be any naturally occurring amino acid
<220> FEATURE:
<221> NAME/KEY: misc_feature
<222> LOCATION: (361)..(363)
<223> OTHER INFORMATION: Xaa can be any naturally occurring amino acid
<220> FEATURE:
<221> NAME/KEY: misc_feature
```

<222> LOCATION: (365)..(365)
<223> OTHER INFORMATION: Xaa can be any naturally occurring amino acid

<400> SEQUENCE: 3

```
Met Thr Lys Xaa Leu Xaa Xaa Xaa Ala Xaa Xaa Xaa Gly Ala Xaa
1               5                   10                  15

Xaa Xaa Xaa Met Pro Xaa Thr Xaa Arg Xaa Gln Gly Xaa Val Xaa Xaa
            20                  25                  30

Val Gly Val Lys Val Xaa Pro Trp Ile Pro Thr Xaa Xaa Xaa Arg Xaa
            35                  40                  45

Leu Xaa Xaa Gly Arg Ser Val Ile Ile Asp Gly Asn Thr Leu Asp Pro
    50                  55                  60

Thr Leu Gln Leu Met Leu Ser Xaa Xaa Arg Xaa Xaa Gly Xaa Asp Gly
65              70                  75                  80

Leu Xaa Val Asp Asp Xaa Xaa Xaa Ser Arg Ala Xaa Met Xaa Xaa
            85                  90                  95

Xaa Xaa Xaa Xaa Xaa Pro Gly Pro Gln Ile His Val Asp Val Xaa Xaa
            100                 105                 110

Leu Xaa Xaa Pro Gly Pro Ala Gly Xaa Ile Pro Ala Arg His Tyr Arg
    115                 120                 125

Pro Xaa Gly Gly Xaa Xaa Gln Xaa Pro Leu Leu Val Phe Tyr His Gly
    130                 135                 140

Gly Gly Trp Xaa Xaa Gly Asp Leu Asp Thr His Asp Xaa Leu Cys Arg
145                 150                 155                 160

Leu Thr Cys Arg Asp Ala Xaa Ile Xaa Val Leu Ser Ile Asp Tyr Arg
                165                 170                 175

Leu Ala Pro Glu His Pro Ala Pro Ala Ala Xaa Xaa Asp Ala Tyr Ala
                180                 185                 190

Ala Phe Xaa Trp Ala His Glu His Ala Xaa Asp Glu Xaa Gly Ala Xaa
            195                 200                 205

Pro Gly Arg Val Ala Val Gly Gly Asp Ser Ala Gly Gly Asn Leu Xaa
    210                 215                 220

Ala Val Val Xaa Gln Leu Ala Arg Asp Xaa Ala Arg Tyr Glu Gly Gly
225                 230                 235                 240

Pro Xaa Pro Val Leu Gln Trp Leu Xaa Tyr Pro Arg Thr Asp Phe Thr
            245                 250                 255

Ala Xaa Thr Arg Ser Xaa Xaa Leu Phe Xaa Xaa Gly Phe Leu Leu Thr
            260                 265                 270

Lys Arg Asp Ile Asp Trp Phe Xaa Xaa Gln Tyr Leu Arg Xaa Ser Xaa
            275                 280                 285

Xaa Asp Xaa Xaa Asp Pro Arg Xaa Ser Pro Xaa Leu Ala Glu Ser Leu
    290                 295                 300

Xaa Gly Leu Ala Pro Ala Leu Ile Ala Val Ala Gly Phe Asp Pro Leu
305                 310                 315                 320

Arg Asp Glu Gly Xaa Ser Tyr Ala Xaa Ala Leu Arg Ala Ala Gly Thr
                325                 330                 335

Xaa Val Asp Leu Arg Tyr Leu Gly Ser Leu Thr His Gly Phe Xaa Asn
            340                 345                 350

Leu Phe Gln Leu Gly Gly Xaa Ser Xaa Xaa Xaa Thr Xaa Glu Leu Ile
            355                 360                 365

Ser Ala Leu Arg Ala His Leu Ser Arg Val
            370                 375
```